United States Patent
Schlossberg et al.

(10) Patent No.: US 11,241,515 B2
(45) Date of Patent: Feb. 8, 2022

(54) CONTROLLED PRODUCTION OF SPHERICAL CALCIUM PHOSPHATE, MAGNESIUM PHOSPHATE, AND STRONTIUM PHOSPHATE PARTICLES FOR DENTAL AND ORTHOPEDIC APPLICATIONS USING DUAL ASYMMETRIC CENTRIFUGATION

(71) Applicant: OSTEONOVUS LLC, Toledo, OH (US)

(72) Inventors: Brian Schlossberg, Boston, MA (US); Olivia Norman, Toledo, OH (US)

(73) Assignee: OSTEONOVUS LLC, Toledo, OH (US)

( * ) Notice: Subject to any disclaimer, the term of this patent is extended or adjusted under 35 U.S.C. 154(b) by 2 days.

(21) Appl. No.: 16/087,757

(22) PCT Filed: Mar. 23, 2017

(86) PCT No.: PCT/US2017/023753
§ 371 (c)(1),
(2) Date: Aug. 6, 2020

(87) PCT Pub. No.: WO2017/165612
PCT Pub. Date: Sep. 28, 2017

(65) Prior Publication Data
US 2020/0222580 A1     Jul. 16, 2020

Related U.S. Application Data

(60) Provisional application No. 62/312,516, filed on Mar. 24, 2016.

(51) Int. Cl.
| | | |
|---|---|---|
| A61L 24/02 | (2006.01) |
| A61L 27/46 | (2006.01) |
| A61L 27/12 | (2006.01) |
| A61L 27/54 | (2006.01) |
| A61L 24/00 | (2006.01) |
| B01J 2/12 | (2006.01) |

(52) U.S. Cl.
CPC ........... *A61L 24/02* (2013.01); *A61L 24/0015* (2013.01); *A61L 24/0084* (2013.01); *B01J 2/12* (2013.01); *A61L 2430/02* (2013.01)

(58) Field of Classification Search
CPC .. A61L 24/02; A61L 24/0015; A61L 24/0084; A61L 27/12; A61L 27/46; A61L 27/54; A61L 2430/02
See application file for complete search history.

(56) References Cited

PUBLICATIONS

International Preliminary Report and Written Opinion, Application No. PCT/US2017/023753, dated Oct. 4, 2018.

*Primary Examiner* — Zohreh A Fay
(74) *Attorney, Agent, or Firm* — Jacob M. Ward; Ward Law Office LLC (57) ABSTRACT

Described is a method for the production of substantially spherical calcium phosphate particles that involves subjecting a composition comprising calcium phosphate to dual asymmetric centrifugation (DAC). Also described are products of the method.

19 Claims, 10 Drawing Sheets

CONTROLLED PRODUCTION OF SPHERICAL CALCIUM PHOSPHATE, MAGNESIUM PHOSPHATE, AND STRONTIUM PHOSPHATE PARTICLES FOR DENTAL AND ORTHOPEDIC APPLICATIONS USING DUAL ASYMMETRIC CENTRIFUGATION

CROSS-REFERENCE TO RELATED APPLICATIONS

This application is the National Phase of International Application PCT/US2017/023753 filed Mar. 23, 2017, which designated the U.S. That International Application was published in English under PCT Article 21(2) on Sep. 28, 2017 as International Publication Number WO 2017/165612A1. PCT/US2017/023753 claims priority to U.S. Provisional Application No. 62/312,516, filed under 35 U.S.C. § 111(b) on Mar. 24, 2016, the entire disclosure of which is incorporated herein by reference for all purposes.

BACKGROUND OF THE INVENTION

Calcium phosphate (CaP) materials have been used for decades as bone graft substitutes in the dental and orthopedic fields. Accordingly, numerous fabrication forms have been proposed and used. Among these forms, putties have good commercial potential because they often have biological properties as desirable as those of CaP granules, but much better handling characteristics. Injectable CaP materials may consist of nanoparticles dispersed in an aqueous solution. After implantation, the CaP is seen as a dense solid by cells. Cell invasion is possible, but requires material displacement or removal. Moldable CaP putties may consist of granules held together by a hydrogel, hence allowing rapid bone in-growth into the space filled with the hydrogel and ceramic resorption throughout the defect.

All CaP forms (injectable, putty, and granules) have a common feature, namely, they consist of solid particles that interact physically and/or chemically during handling. As such, understanding these interactions and controlling the design of CaP particles is important for controlling the handling properties, such as cohesion and injectability, of the CaP. Also, most granular CaP bone graft substitutes have a diameter in the range of 0.5 mm to 5 mm because they should allow blood vessel in-growth in the intergranular space, hence providing rapid ceramic resorption and bone in-growth.

One strategy to improve injectability is to use spherical particles. The injectability of a CaP paste can be enhanced using spherical tetracalcium phosphate particles. Unfortunately, controlled production of spherical calcium phosphate particles remains a challenge. Such spherical particles are important for the synthesis of pastes and cements delivered into the host bone by minimally-invasive approaches. More than a dozen different methods have been used to produce spherical CaP particles. These methods include precipitation, flame synthesis (spray pyrolysis), spray drying, electrospraying, precipitation-emulsification, suspension plasma-spraying (atomization), spray-drying, freeze granulation, drip casting (droplet extrusion), emulsification, hydro-casting, lost wax, spray granulation (high shear mixing), extrusion spheronization, sieve shaking, plasma melting, and combustion flame spraying (flame spheronization). However, there remains a need in the art for better, simpler, and more efficient methods of producing spherical CaP particles.

SUMMARY OF THE INVENTION

The present disclosure relates to methods for the production of spherical calcium phosphate particles for use as bone graft substitutes, especially for use in the dental and orthopedic fields.

Provided herein is a method of producing substantially spherical particles. The method comprises subjecting a composition comprising at least one of calcium phosphate, magnesium phosphate, or strontium phosphate to dual asymmetric centrifugation (DAC) to produce substantially spherical particles. In certain embodiments, the composition comprises a mixture of calcium phosphate and magnesium phosphate. In particular embodiments, the composition comprises monetite and newberyite. In particular embodiments, the composition comprises from about 54% to about 65% by weight monetite, and from about 6% to about 26% by weight newberyite.

In certain embodiments, the DAC comprises a plurality of discrete DAC processing steps that each incorporate 800-1900 revolutions per minute for 20-85 seconds. In certain embodiments, the composition includes a biopolymer. In particular embodiments, the biopolymer comprises carboxymethylcellulose, alginate, chitosan, or combinations thereof. In certain embodiments, the method comprises using the substantially spherical particles in an orthopedic or dental bone graft substitute.

Further provided herein is a method for producing substantially spherical calcium phosphate (CaP), magnesium phosphate (MgP), or strontium phosphate (SrP) particles, the method comprising mixing a dry powder basic anionic reagent with a liquid acidic cationic reagent to produce a slurry, dehydrating the slurry to form a dry cake, subjecting the dry cake to a particle size reduction step to create a fine powder comprising CaP, MgP, or SrP particles, adding an initiator to the fine powder to create a reaction mixture, adding a solution comprising colloidal silica to the reaction mixture to form a paste, and subjecting the paste to dual asymmetric centrifugation (DAC) to produce substantially spherical CaP, MgP, or SrP particles. Also provided are the products of the method.

In certain embodiments, the slurry is dehydrated to ≤1% surface moisture. In certain embodiments, the slurry is dehydrated through one or more dehydration steps selected from the group consisting of: heating in an oven, such as a conventional oven or a vacuum oven; irradiating with microwave radiation; iteratively washing with a low vapor pressure solvent; and lyophilizing by sublimation under vacuum (for instance, at a temperature of less than 50° C.). In certain embodiments, the slurry is dehydrated in an oven. In certain embodiments, the slurry is dehydrated by irradiating the slurry with microwave radiation. In certain embodiments, the slurry is dehydrated by a two-step dehydration process comprising microwave irradiation and drying in an oven. In certain embodiments, the CaP, MgP, or SrP particles in the fine powder have a particle size ranging from about 25 μm to about 250 μm.

In certain embodiments, the initiator comprises MgO, CaO, borax ($NaB_4O_7$), $H_3PO_4$, calcium hydroxide, magnesium hydroxide, sodium hydroxide, a calcium phosphate, poly(methyl methacrylate) (PMMA), a metal or organometallic catalyst, water, or combinations thereof. In certain embodiments, the method further includes homogenizing the reaction mixture. In certain embodiments, the amount of the solution added to the reaction mixture is near the plastic limit of the CaP, MgP, or SrP particles. In certain embodiments, the method further includes adjusting one or more of mixing speed and mixing time of the DAC to control the mean particle diameter of the spherical CaP, MgP, or SrP particles. In certain embodiments, the method further includes using the substantially spherical CaP, MgP, or SrP particles in an orthopedic or dental bone graft substitute.

In certain embodiments, the slurry includes a mixture of calcium phosphate and magnesium phosphate. In certain embodiments, the slurry includes a pH buffer. In certain embodiments, the dry powder is in a co-precipitate of monosodium phosphate ($NaH_2PO_4$) and/or disodium phosphate ($Na_2HPO_4$), and one or more of: $Ca_{10}(PO_4)_6(OH)_2$ (hydroxyapatite), tetracalcium phosphate (TTCP, $Ca_4(PO_4)_2O$), tricalcium phosphate [α-TCP, α-$Ca_2(PO_4)_2$ and β-TCP, β-$Ca_3(PO_4)_2$], dicalcium phosphate anhydrous (DCPA, monetite, $CaHPO_4$), di-calcium phosphate dehydrate (DCPD, brushite, $CaHPO_4.2H_2O$), octacalcium phosphate (OCP, $CaSH_2(PO_4)_6.5H_2O$), $Mg(H_2PO_4)_2$, $MgHPO_4$, $Mg(PO_3OH)_3 . (H_2O)$ (newberyite), $Mg_3(PO_4)_2$, and $Sr_3(PO_4)_2$.

In certain embodiments, the DAC includes a plurality of discrete DAC processing steps, wherein each DAC processing step is conducted with a different mixing time or mixing speed. In particular embodiments, a first DAC processing step is conducted at a mixing speed greater than 1000 rpm, and a second DAC processing step is conducted at a mixing speed less than 1000 rpm. In particular embodiments, each DAC processing step incorporates 800-1900 revolutions per minute for 20-85 seconds. In certain embodiments, the method further includes mixing the substantially spherical CaP, MgP, or SrP particles with carboxymethylcellulose (CMC).

In certain embodiments, the method further includes subjecting the substantially spherical CaP, MgP, or SrP particles to a second dehydration process to produce dehydrated substantially spherical CaP, MgP, or SrP particles. In particular embodiments, the dehydrated substantially spherical CaP, MgP, or SrP particles have <0.5 wt. % residual water. In certain embodiments, the second dehydration process comprises one or more dehydration steps selected from the group consisting of heating in an oven, such as a conventional oven or a vacuum oven; irradiating with microwave radiation; iteratively washing with a low vapor pressure solvent; and lyophilizing by sublimation under vacuum (for instance, at a temperature of less than 50° C.). In particular embodiments, the second dehydration process comprises washing the substantially spherical CaP, MgP, or SrP particles 3-7 times in ethanol, hexane, or acetone. In particular embodiments, the second dehydration process comprises heating the substantially spherical CaP, MgP, or SrP particles in an oven at a temperature above about 75° C. for a time ranging from about 18 hours to about 24 hours. In certain embodiments, the second dehydration process comprises a two-step dehydration process comprising microwave irradiation and drying in an oven.

Also provided is a method of preparing a cement composition, the method comprising preparing a calcium phosphate slurry, subjecting the calcium phosphate slurry to dual asymmetric centrifugation (DAC) to produce substantially spherical calcium phosphate particles, and mixing the substantially spherical calcium phosphate particles with a solution to produce a cement paste which sets into a hardened mass. In certain embodiments, a drug is incorporated into the slurry or the cement paste.

Also provided is a method of preparing a moldable material, the method comprising mixing carboxymethylcellulose with water to form a foam, and mixing the foam with substantially spherical calcium phosphate particles to produce a moldable material, wherein the moldable material is a heterogeneous mixture comprising particles having a size ranging from about 25 µm to about 2 mm. In certain embodiments, the foam comprises 50-99 vol. % entrapped air.

Also provided is a kit comprising a first container housing substantially spherical particles comprising calcium phosphate (CaP) and magnesium phosphate (MgP), where the substantially spherical particles have a size ranging from about 25 µm to about 2 mm, and a second container housing a liquid.

Also provided is a composition comprising substantially spherical calcium phosphate particles having a size ranging from about 25 µm to about 2 mm, and carboxymethylcellulose, wherein the composition is a moldable material.

Also provided is a composition comprising a mixture of calcium phosphate (CaP) particles and magnesium phosphate (MgP) particles, where the CaP particles and the MgP particles are substantially spherical and have a size ranging from about 25 µm to about 2 mm, and a biopolymer, where the composition is a moldable material. In certain embodiments, the biopolymer comprises carboxymethylcellulose, chitosan, alginate, or combinations thereof.

Also provided is a bone graft material comprising a cement composition comprising CaP, MgP, silica, and a biopolymer, where the bone graft material is dehydrated so as to be capable of transforming into a desired shape and size under rehydration. In certain embodiments, the biopolymer comprises carboxymethylcellulose, chitosan, alginate, or combinations thereof.

Various aspects of this invention will become apparent to those skilled in the art from the following detailed description of the preferred embodiment, when read in light of the accompanying drawings.

DETAILED DESCRIPTION

The present disclosure describes methods for the production of spherical calcium phosphate particles using dual asymmetric centrifugation (DAC), especially for use as bone graft substitutes in the dental and orthopedic fields. DAC is a kind of centrifugation in which a container is turned around the main rotational axis with a defined distance and at a defined speed. The main difference between DAC and normal centrifugation is that the container is turned around its own center (vertical axis) during the normal centrifugation process. This results in two overlaying movements of the sample material in the centrifugation container. While the main rotation pushes the sample material in an outward direction in response to centrifugal forces, the rotation of the centrifugation container around its own center pushes the sample in the opposite direction due to adhesion between the sample material and the rotating container. The latter movement (the inward transport of the sample material) is effective if sufficient adhesion of the sample material on the container material is given and if the sample material is sufficiently viscous, because both influence the amount of energy that can be transferred into the sample material.

In the process described herein, a DAC manufacturing of calcium phosphate, magnesium phosphate, and strontium phosphate particles is described. This DAC manufacturing is a kinetic consolidation, milling, and polishing process wherein DAC speeds may be varied for discrete periods of time while the contents of the mixing vessel undergo an acid/base neutralization reaction. The interaction between the independent input variables (e.g., phase composition of the reactants, % crystal water, mixing rpm per step, number of mixing steps, time per step, total elapsed time, etc.) may affect the output variables, such as particle size and mechanical strength, and may therefore be used to controllably produce particles having desired properties.

In one non-limiting example of the process herein, acidic crystalline calcium phosphate and magnesium phosphate salts are combined with basic magnesium oxide salts and colloidal silica solution in water. These materials undergo an acid/base neutralization reaction when mixed. These reactants are then subjected to a discrete series of DAC manufacturing steps for mixing the reactants, particle consolidation, milling, and polishing. In some embodiments, this involves up to 7 discrete steps, where each step incorporates 800-1900 revolutions per minute (RPMs) for 20-85 seconds each.

A high rpm (>1000) is important during the initial stages of DAC manufacturing for reactant mixing, and particle formation/consolidation. A high rpm facilitates both instantaneous mixing of the reactants and concurrent consolidation of particles during the acid/base reaction resulting from the mixing. High rpm during the initial stages of manufacturing results in a population of substantially spherical particles (weighted towards the upper limit of 25 μm-3 mm) with considerable mechanical properties (relative to particles produced using low rpm during the mixing and consolidation steps).

A low rpm (<1000) is important for milling and polishing of the formed particles in the DAC manufacturing process once the particles have been formed. DAC processing of the particles under a low rpm reduces the particle size distribution and polishes the surfaces of the particles to eliminate defects. Thus, in some embodiments, one or more high rpm DAC steps are conducted followed by one or more low rpm DAC steps.

DAC has been known for the rapid mixing of viscous components and is widely used to rapidly mix two-component composites. Since mixing by DAC is significantly fast, the technology offers an efficient improvement for the controlled production of substantially spherical calcium phosphate, magnesium phosphate, and strontium phosphate particles. The term "substantially spherical" as used herein is intended to describe a particle whose shape is nearly or mostly spherical, but which may nonetheless not have an identical radius at all points. In other words, substantially spherical particles may not be perfectly spherical. (Example substantially spherical particles are shown in the SEM images in FIGS. 5-9.)

Figure 1:
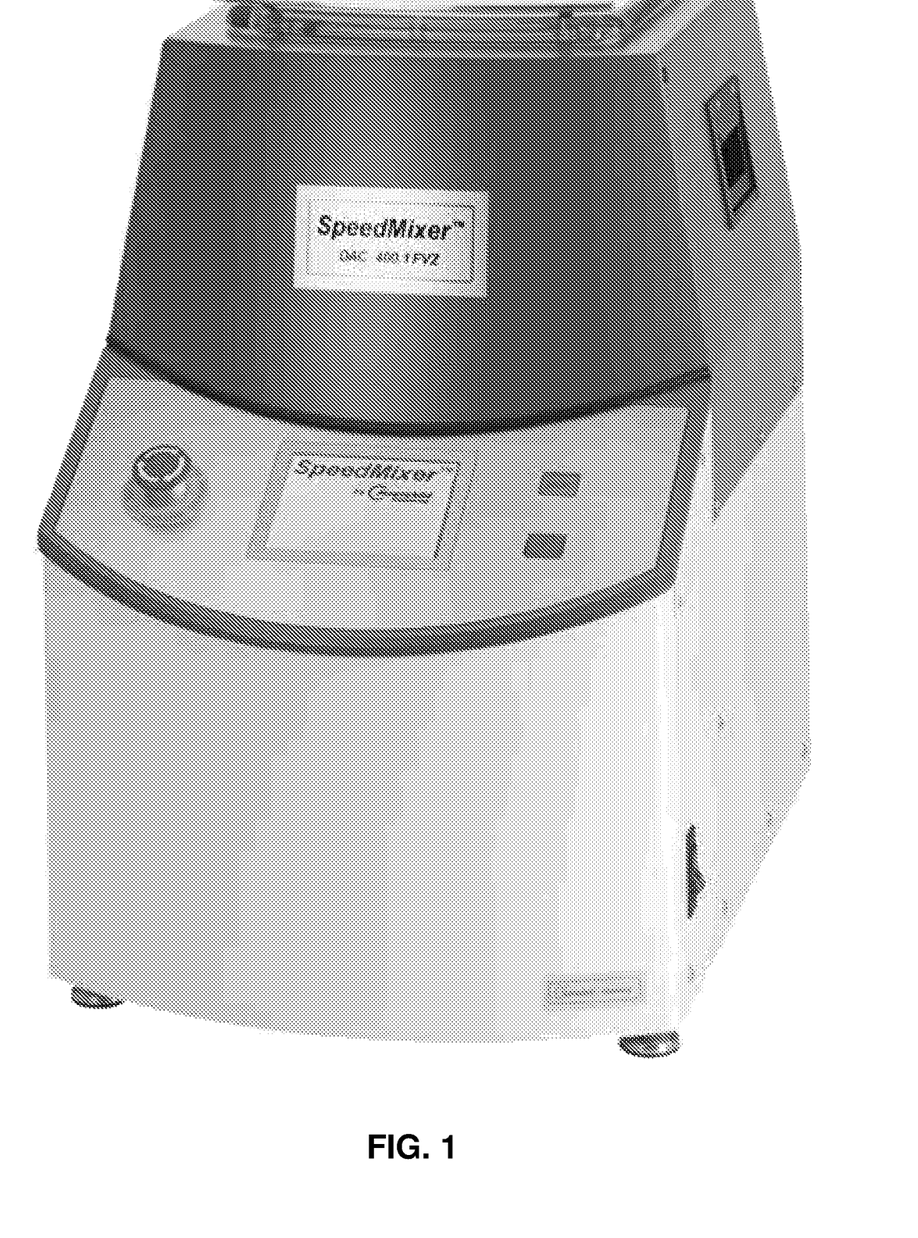
FIG. 1 is a perspective view of a non-limiting example dual asymmetric centrifuge (DAC) that can be used for production of spherical calcium phosphate particles in accordance with the present disclosure.

Referring to the figures, FIG. 1 illustrates a non-limiting example dual asymmetric centrifuge (DAC) that can be used for the production of spherical calcium phosphate particles in accordance with the present disclosure. (A counterweight may be present inside the machine.) The DAC container is turned around the primary axis of rotation with a defined distance and at a defined speed. The DAC container is simultaneously turned around its own center as a secondary axis of rotation. Schematic drawings of the DAC rotational planes are presented in both top view (FIG. 2) and side view (FIG. 3). The defined distance of the primary axis of rotation of the DAC forms an angle of about 40° with the primary rotation plane. However, other angles are possible and are encompassed within the present disclosure. The DAC container rotates along the secondary axis of rotation in the opposite direction of the primary axis of rotation with approximately one-quarter rpm of the frequency of the primary axis of rotation. (For clarity, reference to mixing speed herein is describing the speed of rotation of the primary axis.) Due to the dual rotational axes and the rotational offset angle, the contents of the container are subjected to constant strong shear forces, as depicted in FIG. 4.

Figure 2:
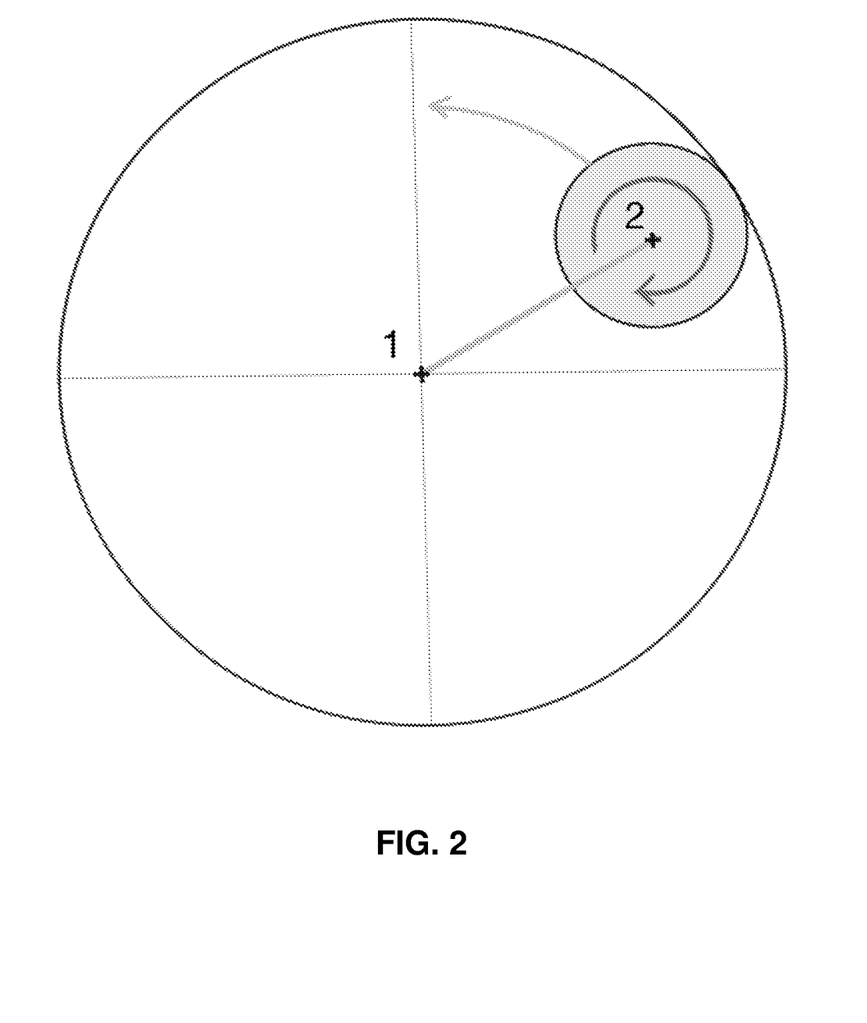
FIG. 2 is a schematic top view of the dual asymmetric centrifuge rotational planes. The DAC container (smaller circle) can be oriented at an angle of about 40° relative to the primary rotation plane (larger circle). The primary axis of rotation (1) allows for maximum speed of 2300 rpm. The secondary axis of rotation (2) allows for fixed speeds of approximately one-quarter of the primary axis rotational speed.
Figure 3:
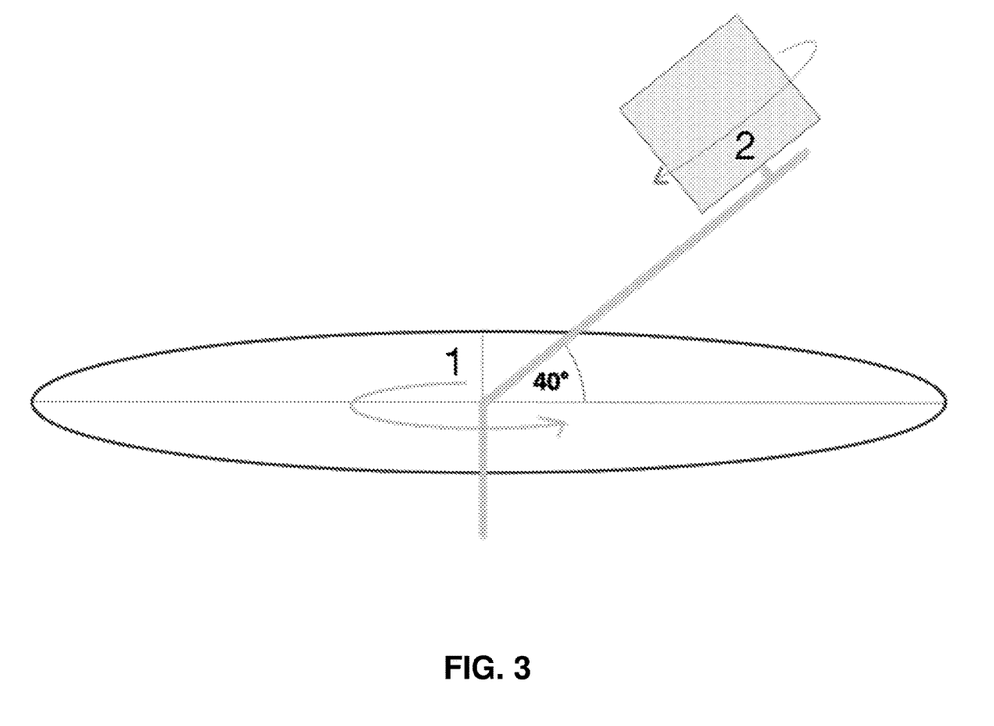
FIG. 3 is a schematic side view of the dual asymmetric centrifuge rotational planes. The DAC container (square shape) can be oriented at an angle of about 40° relative to the primary rotation plane (oval shape). The primary axis of rotation (1) allows for a maximum speed of 2300 rpm. The secondary axis of rotation (2) allows for fixed speeds of approximately one-quarter of the primary axis rotational speed.

FIG. 2 is a schematic top view of a DAC usable for the production of spherical calcium phosphate particles. The DAC container (smaller circle) can be oriented at an angle of about 40° relative to the primary rotation plane (larger circle). The primary axis of rotation 1 allows for maximum speed of 2300 rpm. The secondary axis of rotation 2 allows for fixed speeds of approximately one-quarter of the primary axis rotational speed.

FIG. 3 is a schematic side view of the DAC used for the production of spherical calcium phosphate particles. The DAC container (square shape) can be oriented at an angle of about 40° relative to the primary rotation plane (circle shape). The primary axis of rotation 1 allows for maximum speed of 2300 rpm. The secondary axis of rotation 2 allows for fixed speeds of approximately one-quarter of the primary axis rotational speed.

Figure 4:
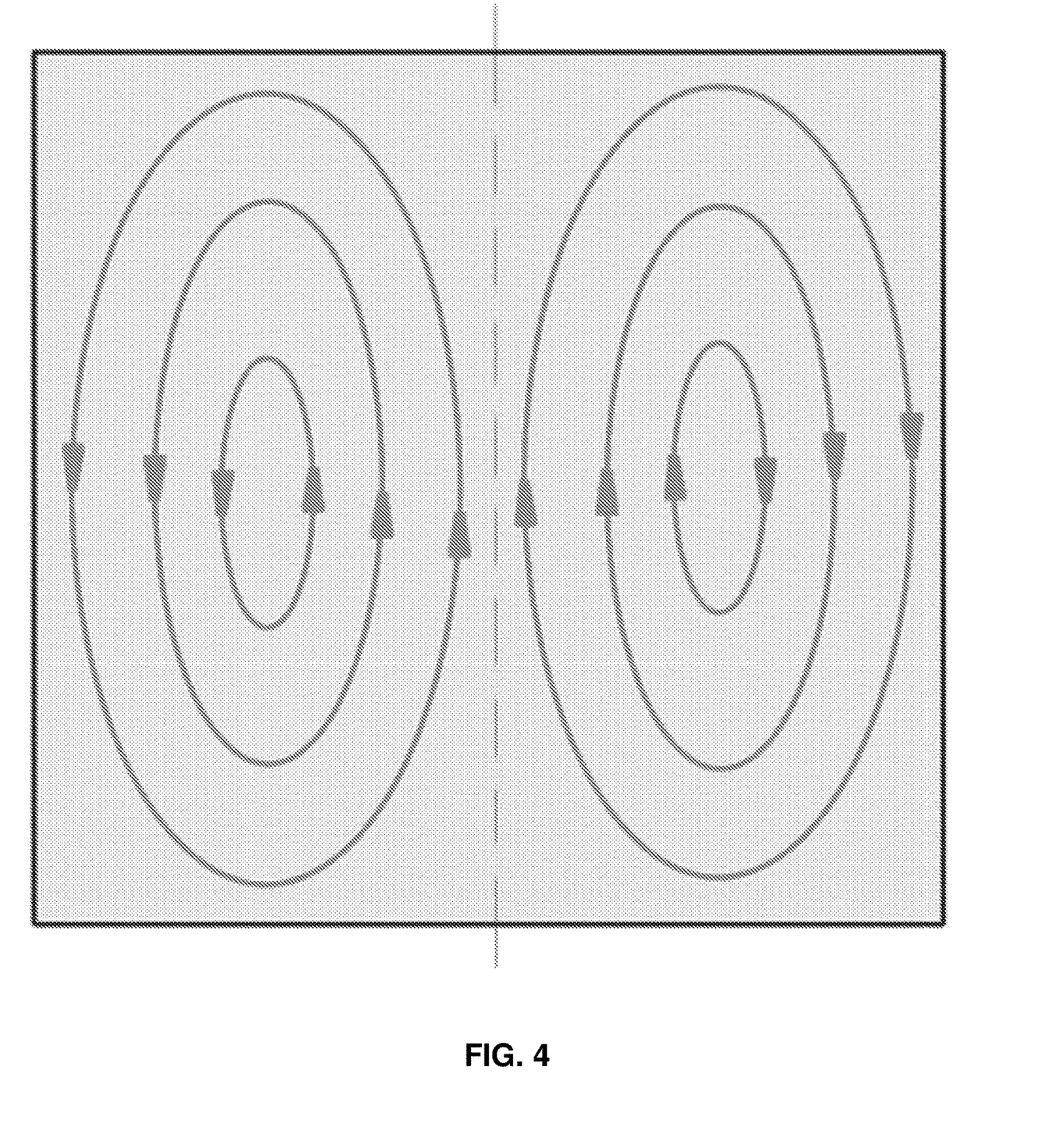
FIG. 4 is a single plane fluid flow diagram that illustrates the mixing pattern of liquid or paste caused by the dual asymmetric centrifuge mixing. Three dimensional flow patterns also include a radial component vector in the plane parallel with the axis of rotation (orthogonal to the plane presented in FIG. 4).
Figure 5:
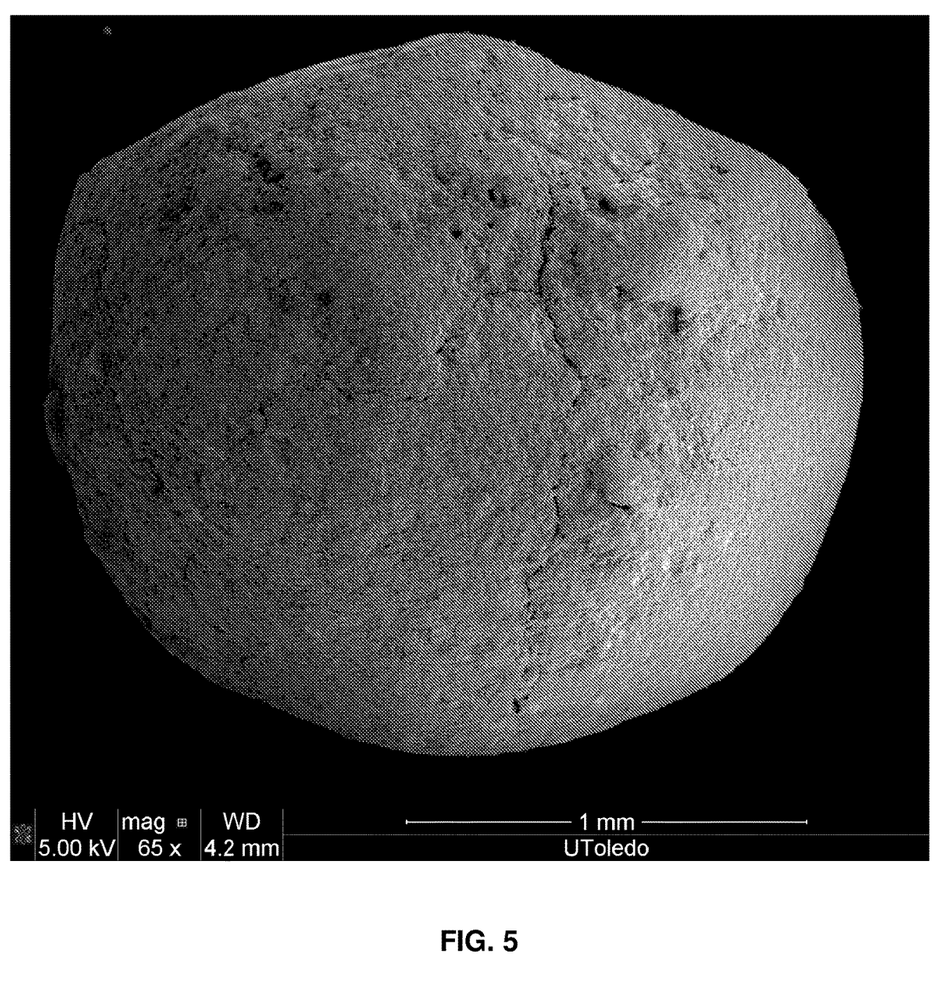
FIG. 5 is a scanning electronic micrograph (SEM) of spherical calcium phosphate particles produced by DAC within the 1 mm<x≤2 mm particle size range. This SEM image is shown at 65× magnification.
Figure 6:
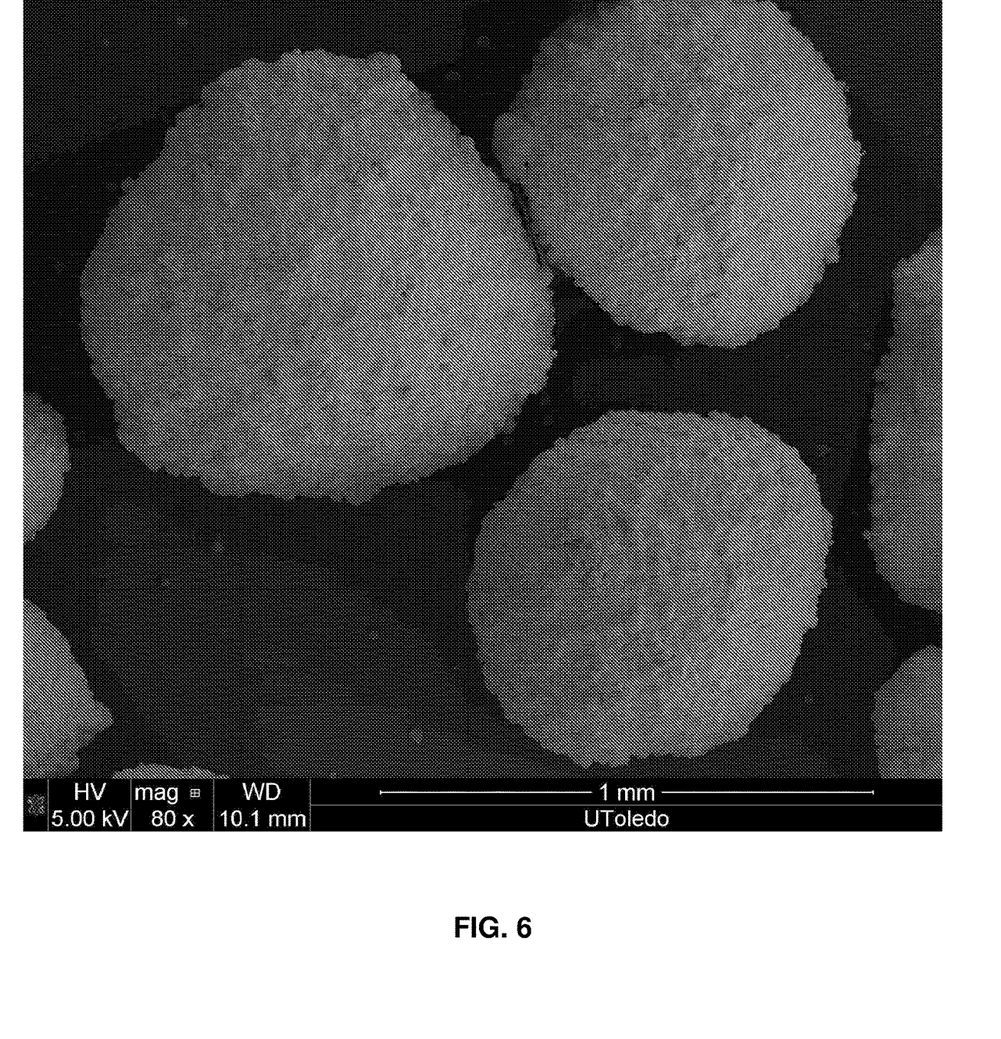
FIG. 6 is a scanning electronic micrograph (SEM) of spherical calcium phosphate particles produced by DAC within the 0.5 mm<x≤1 mm particle size range. This SEM image is shown at 80× magnification.
Figure 7:
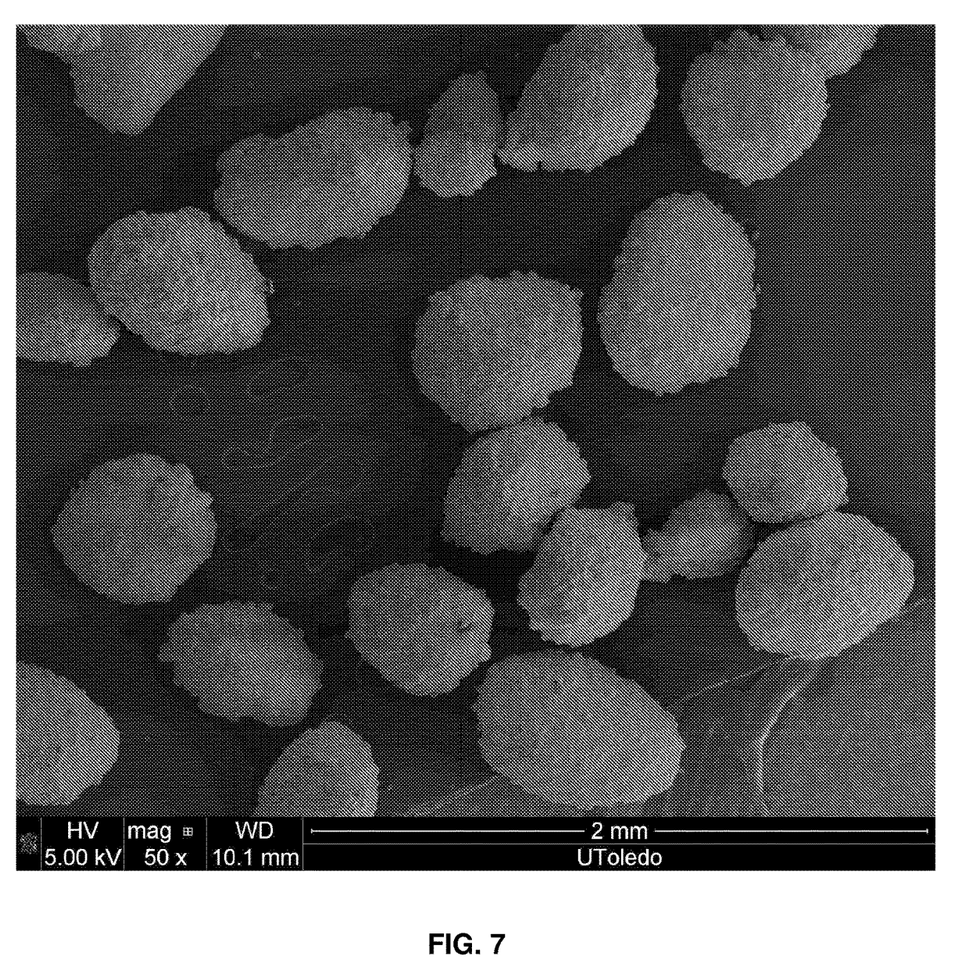
FIG. 7 is a scanning electronic micrograph (SEM) of spherical calcium phosphate particles produced by DAC within the 0.25 mm<x≤0.5 mm particle size range. This SEM image is shown at 50× magnification.
Figure 8:
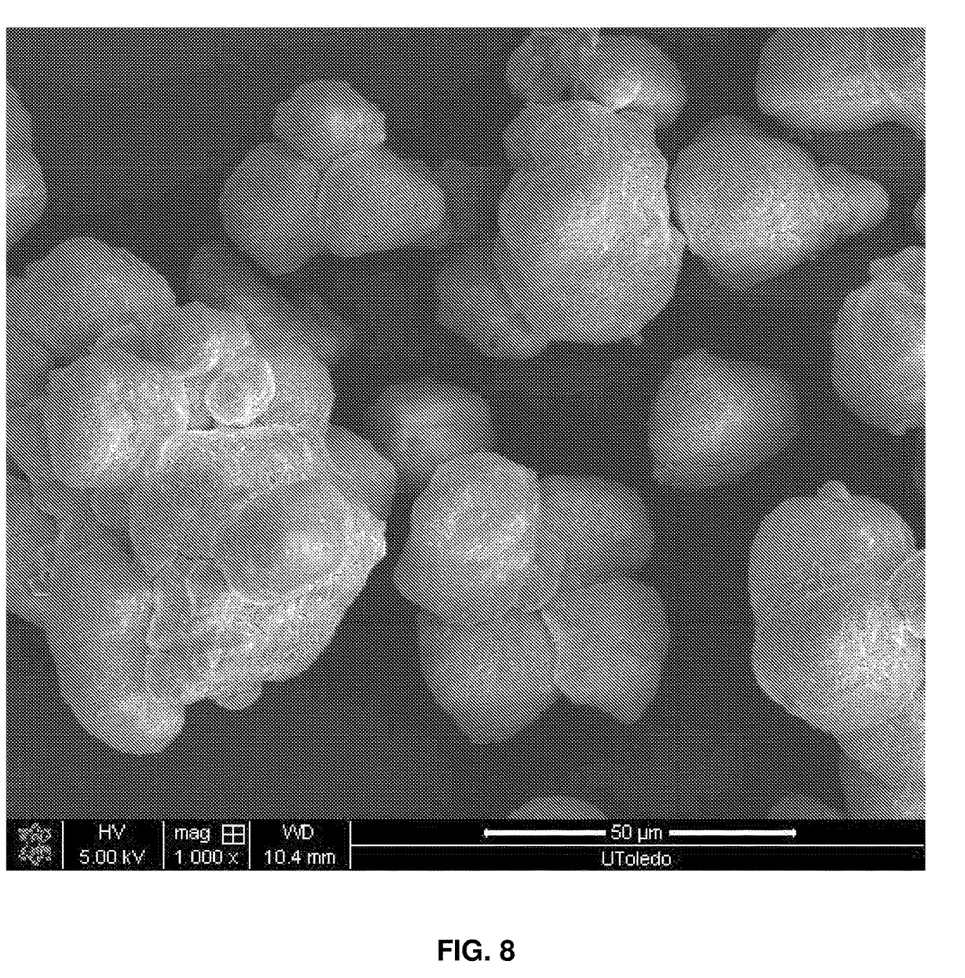
FIG. 8 is a scanning electronic micrograph (SEM) of spherical calcium phosphate particles produced by DAC within the 0.025 mm<x≤0.25 mm particle size range. This SEM image is shown at 1000× magnification.

FIG. 4 is a single plane fluid flow diagram that illustrates the mixing pattern of liquid or paste caused by the DAC mixing. Three dimensional flow patterns also include a radial component vector in the plane parallel with the axis of rotation (orthogonal to the plane presented in the diagram in FIG. 4).

Calcium phosphate (CaP) materials, or similar salts for bone grafting applications in the dental and orthopedic fields, are typically prepared using conventional acid-base wet chemistry methods. For example, monetite (DCPA) cement can be prepared from a single powder component of $Ca(OH)_2$ (which is readily available commercially and relatively inexpensive) and a setting solution of $H_3PO_4$. Upon mixing the powder with the setting solution, a paste is formed by acid-base reaction between the $H_3PO_4$ and the $Ca(OH)_2$. The paste may further include one or more biopolymers, such as a biopolymer incorporated into the $H_3PO_4$ setting solution mixed with the dry powder starting reagent(s). Such a biopolymer can be present in an amount ranging from about 1% to about 5% by weight of the total composition. Suitable biopolymers include, but are not limited to: chitosan [(1-4)-2-amino-2-deoxy-β-D-glucan], carboxymethylcellulose (CMC), alginate, or combinations thereof.

As a non-limiting example, the paste may be formed according to Equation (1), which shows an example stoichiometric acid-base reaction of phosphoric acid (cation) and calcium hydroxide (anion) to form calcium phosphate and water:

$$2H_3PO_4 + 3Ca(OH)_2 = Ca_3(PO_4)_2 + 6H_2O \qquad \text{Equation (1)}$$

Other non-limiting example CaP cement compositions are described in United State Patent Application Publication No. 2015/0005392 A1, which is incorporated herein by reference in its entirety. However, it is understood that the present disclosure is not limited to monetite or to CaP materials formed from the reaction of Equation (1). Rather, monetite and Equation (1) are described merely for exemplary purposes. A wide variety of calcium phosphate materials may be used in, and prepared by, the methods described herein. Alternatively, other phosphate materials, such as magnesium phosphates and strontium phosphates, as well as mixtures of two or more calcium phosphates, magnesium phosphates, and strontium phosphates, can be utilized in the methods described herein. Suitable calcium phosphates include, but are not limited to: $Ca_{10}(PO_4)_6(OH)_2$ (hydroxyapatite), tetracalcium phosphate (TTCP, $Ca_4(PO_4)_2O$), tricalcium phosphate [α-TCP, α-$Ca_2(PO_4)_2$ and β-TCP, β-$Ca_3(PO_4)_2$], dicalcium phosphate anhydrous (DCPA, monetite, $CaHPO_4$), di-calcium phosphate dehydrate (DCPD, brushite, $CaHPO_4 \cdot 2H_2O$), and octacalcium phosphate (OCP, $CasH_2(PO_4)_6 \cdot 5H_2O$). Suitable magnesium phosphates include, but are not limited to: $Mg(H_2PO_4)_2$, $MgHPO_4$, $Mg(PO_3OH)_3 \cdot (H_2O)$ (newberyite), and $Mg_3(PO_4)_2$. Suitable strontium phosphates include, but are not limited to: $Sr_3(PO_4)_2$. Any one or more of these CaP, MgP, and SrP materials can be utilized in the process described herein to produce substantially spherical particles.

Reactions similar to Equation (1) may be employed for alternative salts usable in bone grafting applications. For example, the magnesium phosphate material newberyite may be formed by mixing stoichiometric amounts of $Mg(OH)_2$ with $H_3PO_4$. In one non-limiting example, a mixture of a CaP (e.g., monetite) and a MgP (e.g., newberyite) is subjected to DAC. For ease of explanation herein, the process is often described herein with reference to a "CaP material". However, it is understood that this is merely for exemplary purposes, and that the "CaP material" may be substituted with a MgP material or a SrP material, and further that a "CaP material" may include mixtures of two or more calcium phosphates, magnesium phosphates, and strontium phosphates.

In the DAC process provided herein, once a CaP material, such as the $Ca_3(PO_4)_2$ from Equation (1), is formed, the CaP material is generally subjected to a dehydration step. Given that water is produced in Equation (1), the CaP material is typically formed in a slurry. The slurry is subjected to a dehydration step to reduce the surface moisture. Suitable dehydration steps include, but are not limited to, drying the CaP material in an oven, irradiating the CaP material with microwave radiation, washing the CaP material one or more times with an alcohol (e.g., ethanol) or other low vapor pressure solvent (e.g., hexane, acetone, or the like), or freeze-drying the CaP material. Alcohol washing has been found to result in very rapid dehydration by forming a liquid emulsion. However, any method which results in reduced surface moisture may be utilized in this step. In some embodiments, the surface moisture is reduced to ≤1%. Complete dehydration may result in sub-optimal results, but is nonetheless encompassed within the scope of the present disclosure. Moreover, multiple dehydration methods can be employed in combination to achieve the desired level of dehydration. For example, the CaP material can be irradiated with microwave irradiation for a certain period of time to drive off the bulk of the water, and then dried in a convection oven for a certain period of time to complete the desired amount of drying.

In some embodiments, the dehydrated CaP material, which is also referred to herein as a dry cake, is then subjected to a particle size reduction step. The particle size reduction step can be conducted with any suitable apparatus, including an agate pestle and mortar, a ball mill, a roller mill, a centrifugal-impact mill and sieve, a cutter mill, an attrition mill, a chaser mill, a fluid-energy mill, and/or a centrifugal-impact pulverizer. The particle size reduction step produces a fine powder. In some embodiments, the fine powder contains particles having an average particle size ranging from about 25 μm to about 250 μm. Regardless of the desired particle size, the appropriately sized particles can be separated by collection with a steel mesh sieve or other suitable method.

The resulting dried fine powder, preferably having an average particle size ranging from about 25 μm to about 250 μm, is mixed with a reaction initiator to initiate the cement reaction (where the reacting composition is referred to as the reaction mixture). The identity of the reaction initiator depends on various factors such as the identity of the CaP composition, the type of reaction being used to form the CaP material, and the desired cement characteristics. Suitable reaction initiators may include: oxides, such as MgO or CaO; phosphates, such as $H_3PO_4$, or additional calcium phosphates; carbonates, such as calcium carbonate; borax ($NaB_4O_7$); hydroxides, such as calcium hydroxide, magnesium hydroxide, or sodium hydroxide; polymers, such as poly(methyl methacrylate) (PMMA); metal or organometallic catalysts; water; or combinations thereof. In one non-limiting example, magnesium oxide (MgO) having a particle size of 99%<150 µm is used as the reaction initiator. Without wishing to be bound by theory, it is believed that adding MgO can create MgP crystals in the mixture which act as seeds for the setting reaction. Upon adding the reaction initiator to the dried fine powder, the cement reaction is initiated. In some embodiments, the reaction mixture is homogenized before further use or processing.

The reaction mixture may optionally include pH buffers. For instance, the dry powder components may comprise a co-precipitate of dicalcium phosphate anhydrite (monetite, $CaHPO_4$) and a pH buffer such as monosodium phosphate ($NaH_2PO_4$), where the $NaH_2PO_4$ is present in small quantities as a pH buffer to prevent the formation of brushite during manufacturing. Though $NaH_2PO_4$ is described for exemplary purposes, any suitable pH buffer can be utilized if a particular pH range of the reaction mixture is desired. For example, disodium phosphate ($Na_2HPO_4$) can also be used as a pH buffer. Similarly, though monetite is described for exemplary purposes, the co-precipitate may include any calcium phosphate, magnesium phosphate, or strontium phosphate, including one or more of: $Ca_{10}(PO_4)_6(OH)_2$ (hydroxyapatite), tetracalcium phosphate (TTCP, $Ca_4(PO_4)_2O$), tricalcium phosphate [α-TCP, α-$Ca_2(PO_4)_2$ and β-TCP, β-$Ca_3(PO_4)_2$], dicalcium phosphate anhydrous (DCPA, monetite, $CaHPO_4$), di-calcium phosphate dehydrate (DCPD, brushite, $CaHPO_4.2H_2O$), octacalcium phosphate (OCP, $CasH_2(PO_4)_6.5H_2O$), $Mg(H_2PO_4)_2$, $MgHPO_4$, $Mg(PO_3OH)_3 \cdot (H_2O)$ (newberyite), $Mg_3(PO_4)_2$, and $Sr_3(PO_4)_2$.

The reaction mixture, preferably homogenized, can either be subjected to DAC directly or first combined with one or more optional additives to adjust various properties of, or add a therapeutic benefit to, the resulting materials. Non-limiting examples of suitable additives include: proteins, osteoinductive and/or osteoconductive materials, silica (such as colloidal silica, or nanosilica sol), X-ray opacifying agents such as strontium phosphate or strontium oxide, medicaments, supporting or strengthening filler materials, crystal growth adjusters, viscosity modifiers, pore-forming agents, antibiotics, antiseptics, growth factors, chemotherapeutic agents, bone resorption inhibitors, color change agents, immersing liquids, carboxylates, carboxylic acids, α-hydroxyl acids, metallic ions, or mixtures thereof. Other suitable additives include substances that adjust setting times (such as pyrophosphates or sulfates), increase injectability or cohesion (such as hydrophobic polymers like collagen), alter swelling time, or introduce macroporosity (such as porogens). It is understood that the additives may be added to the reaction mixture, or may be present in a powder mixture with CaP prior to the reaction initiator being added.

In one non-limiting example, colloidal silica and/or ultrapure deionized water are added to the reaction mixture prior to DAC processing. For instance, small amounts of colloidal silica ($SiO_2$) and magnesium oxide (MgO) can be added to a co-precipitate of $CaHPO_4$ and $NaH_2PO_4$, and the resulting mixture is then processed under DAC to form substantially spherical particles. The concentration of colloidal silica and the total volume of liquid affect the rheological properties of the resulting dry powder/solution mixture (paste). In general, the liquid amount should be near the plastic limit of the CaP powder. The plastic limit is defined as the minimum amount of liquid that must be added to a powder to form a paste. However, the plastic limit may vary by CaP powder due to physiochemical differences (phase, % crystallinity, particle size, surface area, etc.), and small deviations from this limit may provoke noticeable changes in the paste viscosity. The rheological properties of the paste may impact the sphere production, so the concentrations of silica and water should be calibrated to the particular CaP powder.

The reaction mixture, optionally containing one or more additives, is subjected to one or more DAC processing steps. This can be, for example, a plurality of discrete DAC processing steps (for example, from 2 discrete DAC steps to 10 discrete DAC steps), each at different mixing speeds and for different mixing times. However, each DAC processing step is conducted at a mixing speed ranging from about 800 rpms to about 1900 rpms, and for a duration ranging from about 20 seconds to about 85 seconds. In some embodiments, only a single DAC processing step is used. In some embodiments where a plurality of DAC processing steps is utilized, each successive DAC processing step utilizes a lower mixing speed. In other embodiments where a plurality of DAC processing steps is utilized, the first DAC processing step uses a higher mixing speed than the last DAC processing step, but the mixing speeds are varied non-monotonically between the first and last DAC processing steps. In other embodiments where multiple DAC processing steps are utilized, each DAC processing step is conducted at substantially the same mixing speed, though one or more other parameters such as mixing temperature or mixing time are varied.

Suitable commercially available DAC systems include, but are not limited to, Flacktek SpeedMixers™, which include DAC 150 Series mixers, the DAC 250 Mixers, the DAC 400 Mixers, the DAC 600 Mixers, the DAC 800 Mixers, the DAC 1100 Mixers, DAC 3000 HP mixers, and DAC 5000 HP mixers. Commercially available DAC systems are generally sold in size ranges capable of processing samples from 100 g-10 kg. Various containers, including certain polypropylene jars, are specifically designed for use with DAC, and can be used to mix any additives with the reaction mixture prior to dual asymmetric centrifugation. The total amount of contents within the DAC jar is a variable that is important for efficient mixing (the mixing pattern is depicted in FIG. 4) and should be properly calibrated to the jar size and axes of rotation for optimal results. If the center of mass of the jar contents sits at or above the center of the flow diagram, then the contents will be accelerated out of the flow pattern (typically against the lid of the jar) and will not be dispersed within the paste.

When using a combination of two or more phosphate materials, the phase compositions of the acidic phosphate salts are important for producing substantially spherical particles under DAC manufacturing. For example, when using a mixture of monetite and newberyite, the crystallinity (as measured by powder x-ray diffraction) of the monetite and newberyite salts should be within the following ranges for the production of substantially spherical particles: 54%≤x≤63% crystalline monetite (by weight), and 6%≤x≤26% crystalline newberyite (by weight).

Without wishing to be bound by theory, it is believed that the magnesium phosphate phase (e.g., newberyite), when present, incorporates water molecules in the crystalline framework. This crystallized water affects the crystalline properties of the newberyite (crystal size and shape), and these properties play an important role in the formation of substantially spherical particles during DAC manufacturing. When a magnesium phosphate is present, the reaction mixture should contain ≥2% magnesium phosphate (e.g., newberyite) crystallized water (calculated as % wt magnesium phosphate) for optimal results. This crystallized water can be removed by heating the magnesium phosphate sample above 81-85° C. (e.g., during oven drying).

The particles immediately produced from the DAC process are generally soft and still subject to change in shape and size for a short time period. The transition from soft to a hard state, known as consolidation, is important to obtain non-agglomerated well-defined spheres. To facilitate this process, the particles may be subjected to another dehydration step. Thus, following DAC processing, the powder particles should be dried to remove all residual surface and bulk water. Removal of the high-vapor pressure solvent (water) is important to ensure the requisite mechanical properties of the substantially spherical particles for use in orthopedic bone grafting. The preferred drying methods, at least when the product is to be used in orthopedic bone grafting, result in <0.5 wt. % residual water. As with the first dehydration step, this may be accomplished through any suitable means which reduces the surface moisture of the particles. Suitable dehydration methods include, but are not limited to: drying the particles in an oven (for instance, in a conventional oven at a temperature of from about 75° C. for about 18-24 hours), irradiating the particles with microwave radiation, iteratively washing (e.g., washing 3 to 7 times) the particles with a low vapor pressure solvent (e.g., ethanol, hexane, acetone, or the like), or lyophilizing (i.e., freeze-drying) the particles by sublimation under vacuum at temperature of less than 50° C. In some embodiments, the particles are dehydrated to ≤1% surface moisture.

Following dehydration, substantially spherical particles can be recovered. The substantially spherical particles resulting from DAC may include agglomerates of the primary CaP particles dispersed in the mixture, and may include substantially spherical particles ranging in size. In one non-limiting example, the method produces substantially spherical particles having sizes of 1-2 mm, 0.5-1 mm, 0.25-0.5 mm, 0.025-0.25 mm, and ≤0.025 mm. If a particular size range is desired, the particles can be sorted and selected accordingly using, for instance, mesh sieves. Moreover, the DAC can be stopped at a desired point to prevent the formation of clumps. Furthermore, the DAC process provides control over the parameters of the resulting particles. The final mean particle diameter ($d_f$) can be controlled by changing the mixing speed (rpm) and mixing time (t) of the DAC, as defined by the relationship in Equation (2), which shows the relationship between final mean particle diameter ($d_f$), DAC mixing speed (rpm), and DAC mixing time (t):

$$1/d_f = rpm \times t \qquad \text{Equation (2)}$$

Thus, at higher rpm, $d_f$ decreases for a constant t. Similarly, at higher t, $d_f$ decreases for any constant rpm. Therefore, the DAC processing steps can be utilized to controllably increase or decrease the mean particle diameter of CaP, MgP, or Sr particles by adjusting the mixing time and/or mixing speed, where each of the mixing time and the mixing speed is inversely proportional to the resulting mean particle diameter. Other parameters, such as the mixing temperature, may also be adjusted.

It is understood that the above-described process includes various unnecessary optimizations. For example, it is possible to simply subject any reaction mixture in which CaP, MgP, or SrP particles are forming to DAC. For instance, a Ca(OH)$_2$ powder may be mixed with a H$_3$PO$_4$ setting solution, and promptly subjected to DAC instead of first being particle-selected, dehydrated, and then initiated. Though this may result in sub-optimal compositions with fewer than desired spherical particles, it is entirely within the scope of the present disclosure.

The DAC process effectively takes salts which would set on their own and subjects them to DAC to produce a desirable particle distribution. While DAC is quick and easy, other processes produce loosely packed particles which need heat treatments to be made harder. However, certain CaP materials cannot undergo heat treatments because they will decompose. Therefore, DAC, which makes the particles hard upon formation instead of requiring a subsequent heat treatment, is superior to other processes for CaP materials. DAC can create very hard particles—harder particles than can be produced by other processes. DAC also creates very homogenous mixtures.

In general, the substantially spherical particles produced by the DAC process are advantageously used in a wide variety of CaP materials and applications, for instance to prepare a CaP paste having improved injectability. The substantially spherical CaP particles may be used in any application as a CaP starting material. For example, the substantially spherical CaP particles can be combined with a setting solution containing H$_3$PO$_4$ to create a cement paste which sets into a hardened mass. This cement paste may further include any of the biopolymers or other additives (such as drugs) discussed above. Because substantially spherical particles are used to create the paste, it is more easily injectable. The cement may then be used for repairing a wide variety of orthopedic and dental conditions. For example, the cement may be injected into the vertebral body for treatment of spinal fractures, injected into long bone or flat bone fractures to augment the fracture repair or to stabilize the fractured fragments, injected into intact osteoporotic bones to improve strength, used to augment a bone-screw or bone-implant interface, formed into bone-filling granules to replace demineralized bone matrix materials, used as a scaffold support for various types of vertebral fractures, or used in tibia plateau reconstruction, wrist fracture reconstruction, calcaneal reconstruction, or prophylaxis strengthening of the hip bone. The cement may be used as a bone filler in areas of the skeleton where bone may be deficient. In this context, the cement may be used to fill, augment, and/or reconstruct maxillofacial osseous bone defects, including periodontal, oral, and cranio-maxillofacial applications. The cement can be packed gently into bony voids or gaps of the skeletal system (i.e., extremities, pelvis, and spine), including in postero-lateral spinal fusion or vertebral augmentation procedures with appropriate stabilizing hardware. The cement may be used to fill defects which were surgically created osseous defects or osseous defects created from traumatic injury to the bone.

Phosphate compositions, such as cements, formed with the substantially spherical particles made from the DAC process described herein, may be used to form a coating on, for instance, titanium implants, and/or as delivery vehicles for drugs, genes, proteins, cells, DNA, or other molecules. A drug can be dissolved in a CaP paste, or a CaP composition (before or after it sets) can be soaked in a solution comprising a drug, before the CaP material is injected or placed into or onto a desired anatomical location. The drug can then be released into the subject from the cement matrix. Embodiments resulting in sustained release of drugs are also envisioned, for instance by coating the CaP matrix with polymers including PLA/PGA, polyacrylic acid, hydroxyl methylcellulose, and/or chitosan.

Cements formed from the substantially spherical particles may be packaged as a powder mixture which is later mixed with a solvent to make slurry or putty, or as a pre-mixed putty which may a contain nonaqueous extender, e.g., glycerine and/or propylene glycol. The pre-mixed putty allows the cement to set upon contact with water.

In some embodiments, the substantially spherical particles produced by the DAC manufacturing process described herein may be mixed heterogeneously during the filling/packaging process with a biopolymer, such as dry sodium carboxymethyl cellulose (CMC) powder, to enhance the handling properties of the final mixed orthopedic bone graft. These dry powders can be mixed intraoperatively with water using a supplied mixing system prior to implantation to form a moldable cohesive putty-like graft. The DI $H_2O$ should be measured using a graduated syringe, according to the instructions for use for the appropriate device size, and combined with the dry powder components within the mixing system. The mixing system facilitates proper rehydration and homogenous dispersion of the CMC carrier amongst the particles, which produces a moldable and cohesive final mixed graft that is resistant to surgical lavage. After completion of mixing, the putty may be extruded from the mixing system and handled prior to implantation in the intended surgical site.

Alternatively, the substantially spherical particles may be mixed with a biopolymer such as CMC, alginate, or chitosan, then with DI $H_2O$, and then subjected to another dehydration step to produce a dehydrated bone graft material capable of transforming into a desired shape and size upon rehydration. Any of the previously described dehydration steps can be utilized for this purpose.

As another alternative, an advantageous embodiment includes methods of manufacturing/processing that eliminate the need for the end-user to measure the liquid component and mix the dry/liquid components within a mixing system (that facilitate proper rehydration and homogenous dispersion of the CMC carrier amongst the particles). For example, the dry CMC powders may be mixed with water during manufacturing to create a stable biodegradable foam with 50-99 vol. % entrapped air. Preferred foam formulations have an expansion ratio of 2-100× and comprise 250,000-700,000 Dalton CMC. The broad operative range for foam composition allows incorporating to 0.1 to 25 wt. % CMC; 0 to 30% surfactant or wetting agent; 0 to 20 wt. % crosslinking agent for the CMC; and 25 to 99 wt. % water. Generally, higher molecular weight CMC requires lower amounts of cross linker than lower molecular weight CMC in order to obtain foam with the same degree of volumetric expansion. Variable amounts of water are added depending upon the total foam formulation. The CMC foam is then combined with the substantially spherical particles to form a heterogeneous mixture. The broad range of particle size allows incorporating 25 µm-2 mm particles. This mixture is then molded into various shapes (including, but not limited to, rectangular strips, boats, cylinders, cubes, etc.) and rapidly dehydrated using methods that preserve the volume of entrapped air within the foam. These methods may include, but are not limited to, sublimation of water by lyophilizing, or liquid-liquid emulsification using a lower vapor-pressure solvent (e.g., ethanol, hexane, acetone, or the like). The preferred foam shape formulations may be rehydrated intraoperatively with sterile water, saline, blood, or bone marrow aspirate within 0.1-10 minutes to form a moldable cohesive final mixed graft that is resistant to surgical lavage.

Though CMC is often described herein for exemplary purposes, one or more other biopolymers (e.g., alginate, chitosan, etc.) can be mixed with the substantially spherical particles. The biopolymer(s), if present, can further enhance the mechanical properties of the resulting cement by providing a toughening mechanism against the propagation of a crack. The biopolymer(s) can also contribute to the resulting cement composition's injectability, bioactivity, cohesiveness, and improved mechanical properties.

It is also contemplated that compositions formed from the substantially spherical particles may be made available to practitioners such as surgeons, veterinarians, or dentists via a kit containing one or more key components. A non-limiting example of such a kit comprises dry (e.g., a powder containing the substantially spherical particles) and liquid components in separate containers, where the containers may or may not be present in a combined configuration. Many other kits are possible, such as kits comprising a pre-mixed putty instead of the powder and setting solution, and kits including a syringe or multiple syringes for injecting a bone cement composition formed from the components of such kit. Another non-limiting example of a kit includes a heterogeneous mixture of substantially spherical CaP particles, CMC, and DI water in separate containers. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The dry powder basic OH anionic reagents $Ca(OH)_2$ and $Mg(OH)_2$ were mixed stoichiometrically with the liquid acidic $H^+$ cationic reagent $H_3PO_4$ and a pH buffer (sodium bicarbonate) in a reaction vessel using a variable speed overhead mixer. The resulting slurry was dehydrated to ≤1% surface moisture using an oven to form a dry cake. The cake was then milled to create a fine powder, and the 25 µm≤x<250 µm particle size was collected using stainless steel mesh sieves. The dried fine CaP+MgP powder (containing a mixture of monetite and newberyite) was added to an empty beaker. Magnesium oxide (MgO, particle size: 99%<150 µm) powder was added to the beaker containing the powder to initiate the cement reaction. The MgO did not exceed 5.0% by mass, as this may cause the spherical particles to become expansive. The resulting dry powder mixture (containing CaP, MgP, and MgO) was homogenized.

A solution comprising colloidal silica and ultrapure deionized water was prepared in a 968 ml polypropylene jar (11.2 cm diameter×10.4 cm height) that is specially designed for use with DAC. The dry powder mixture was added to the polypropylene DAC jar containing the silica solution. The polypropylene jar was closed using an appropriate cap and placed in the DAC. The DAC used in this example was a machine commercial available under the trade name Speed-Mixer™, as depicted in FIG. 1. The DAC system used was capable of processing samples up to 500 g. The reaction mixture was subjected to 7 discrete DAC processing steps, where a high rpm (>1000) was used in the initial DAC steps and a low rpm (<1000) was used in the later DAC steps.

Immediately following particle formation from the DAC, the particles were still soft, and their shape and size were subject to change. The transition from soft to a hard state, known as consolidation, is important to obtain non-agglomerated well-defined spheres. Therefore, the particles were dehydrated using an oven to ≤1% surface moisture.

Figure 9:
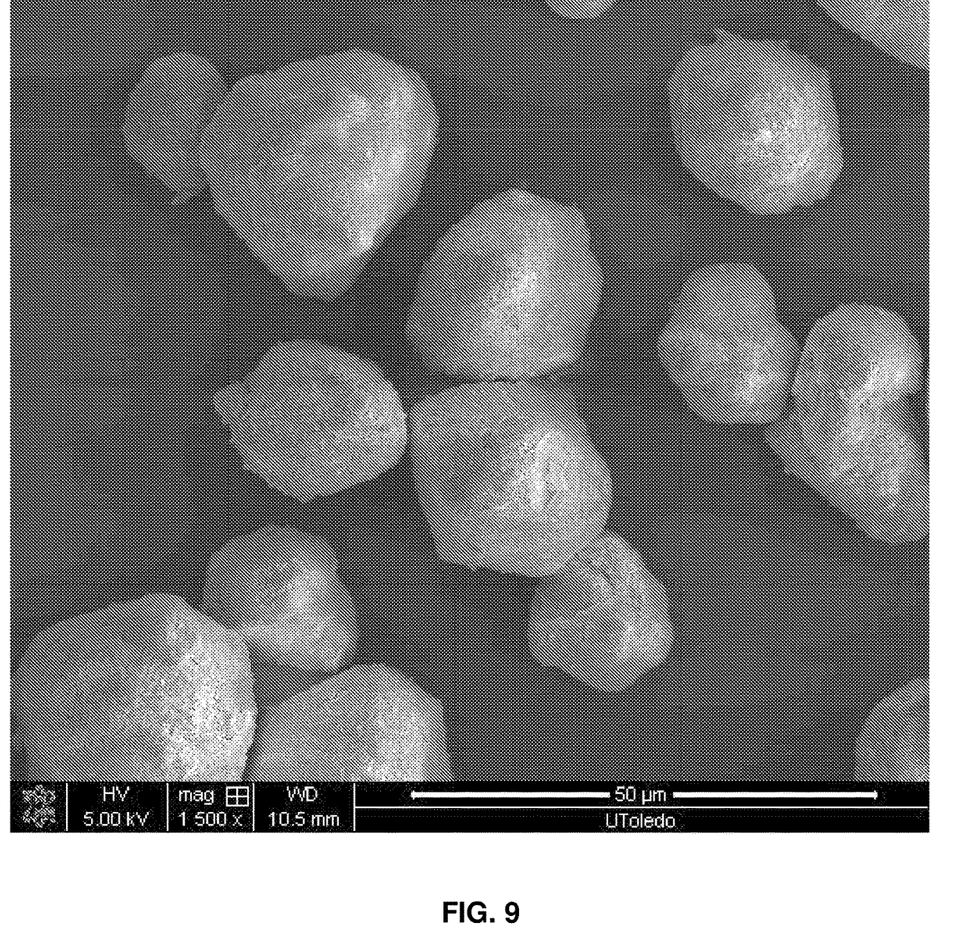
FIG. 9 is a scanning electronic micrograph (SEM) of spherical calcium phosphate particles at produced by DAC within the x≤0.025 mm particle size range. This SEM image is shown at 1500× magnification.

The substantially spherical particles resulting from the DAC process included agglomerates of the primary CaP particles dispersed in the mixture, and their diameter was a few orders of magnitude bigger than the diameter of the primary particle. FIGS. 5-9 show scanning electron micrographs of the spherical calcium phosphate particles produced by this DAC process, presented by particle size range: 1 mm<x≤2 mm (FIG. 5); 0.5 mm<x≤1 mm (FIG. 6); 0.25 mm <x≤0.5 mm (FIG. 7); 0.025 mm<x ≤0.25 mm (FIG. 8); and x≤0.025 mm (FIG. 9).

Figure 10:
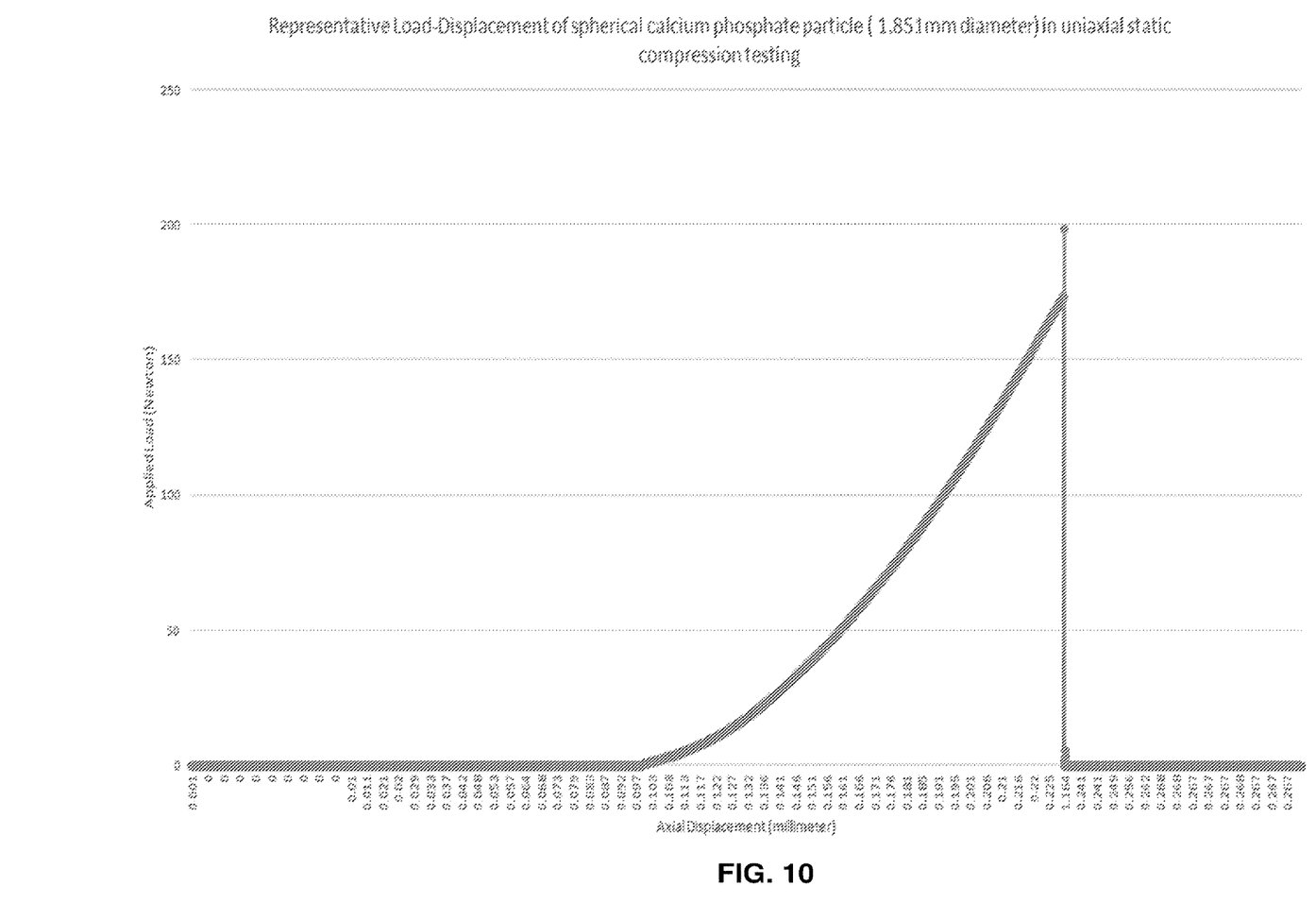
FIG. 10 shows the results of mechanical testing of an example substantially spherical particle having a diameter of 1.851 mm.

FIG. 10 shows the results of mechanical testing of the substantially spherical particles, for an example particle having a diameter of 1.851 mm. As seen from FIG. 10, the process produced particles with a desirable compressive strength for their size.

The principle and mode of operation of this invention have been explained and illustrated. However, it must be understood that this invention may be practiced otherwise than as specifically explained and illustrated without departing from its spirit or scope.

What is claimed is:

1. A method of producing substantially spherical particles, the method comprising:
    subjecting a powder composition comprising magnesium phosphate and at least one of calcium phosphate or strontium phosphate, to dual asymmetric centrifugation (DAC) to produce substantially spherical particles.

2. The method of claim 1, wherein the composition comprises a mixture of calcium phosphate and magnesium phosphate.

3. A method of producing substantially spherical particles, the method comprising:
    subjecting a composition comprising at least one of calcium phosphate, magnesium phosphate, or strontium phosphate, to dual asymmetric centrifugation (DAC) to produce substantially spherical particles;
    wherein the composition comprises a mixture of calcium phosphate and magnesium phosphate; and
    wherein the composition comprises monetite and newberyite.

4. The method of claim 3, wherein the composition comprises from about 54% to about 65% by weight monetite, and from about 6% to about 26% by weight newberyite.

5. A method for producing substantially spherical calcium phosphate (CaP), magnesium phosphate (MgP), or strontium phosphate (SrP) particles, the method comprising:
    mixing a dry powder basic anionic reagent with a liquid acidic cationic reagent to produce a slurry;
    dehydrating the slurry to form a dry cake;
    subjecting the dry cake to a particle size reduction step to create a fine powder comprising CaP, MgP, or SrP particles;
    adding an initiator to the fine powder to produce a reaction mixture;
    adding a solution comprising colloidal silica to the reaction mixture to form a paste, wherein the amount of the solution added to the reaction mixture is near the plastic limit of the CaP, MgP, or SrP particles; and
    subjecting the paste to dual asymmetric centrifugation (DAC) to produce substantially spherical CaP, MgP, or SrP particles.

6. The method of claim 5, wherein the slurry is dehydrated to ≤1% surface moisture.

7. The method of claim 5, wherein the slurry is dehydrated through one or more dehydration steps selected from the group consisting of: heating in an oven; irradiating with microwave radiation; iteratively washing with a low vapor pressure solvent; and lyophilizing by sublimation under vacuum.

8. The method of claim 5, wherein the slurry is dehydrated by a two-step dehydration process comprising microwave irradiation and drying in an oven.

9. The method of claim 5, wherein the slurry is dehydrated by washing the slurry 3-7 times in ethanol, hexane, or acetone.

10. The method of claim 5, wherein the slurry is dehydrated by heating the slurry in an oven at a temperature above about 75° C. for a time ranging from about 18 hours to about 24 hours.

11. The method of claim 5, further comprising adjusting one or more of mixing speed and mixing time of the DAC to control the mean particle diameter of the substantially spherical CaP, MgP, or SrP particles.

12. The method of claim 5, wherein the slurry comprises a co-precipitate of monosodium phosphate ($NaH_2PO_4$) and/or disodium phosphate ($Na_2HPO_4$), and one or more of: $Ca_{10}(PO_4)_6(OH)_2$ (hydroxyapatite), tetracalcium phosphate (TTCP, $Ca_4(PO_4)_2O$), tricalcium phosphate [α-TCP, α-$Ca_2(PO_4)_2$ and β-TCP, β-$Ca_3(PO_4)_2$], dicalcium phosphate anhydrous (DCPA, monetite, $CaHPO_4$), di-calcium phosphate dehydrate (DCPD, brushite, $CaHPO_4.2H_2O$), octacalcium phosphate (OCP, $Ca_8H_2(PO_4)_6.5H_2O$), $Mg(H_2PO_4)_2$, $MgHPO_4$, $Mg(PO_3OH)_3.(H_2O)$ (newberyite), $Mg_3(PO_4)_2$, and $Sr_3(PO_4)_2$.

13. A method for producing substantially spherical calcium phosphate (CaP), magnesium phosphate (MgP), or strontium phosphate (SrP) particles, the method comprising:
    mixing a dry powder basic anionic reagent with a liquid acidic cationic reagent to produce a slurry;
    dehydrating the slurry to form a dry cake;
    subjecting the dry cake to a particle size reduction step to create a fine powder comprising CaP, MgP, or SrP particles;
    adding an initiator to the fine powder to produce a reaction mixture;
    adding a solution comprising colloidal silica to the reaction mixture to form a paste; and
    subjecting the paste to dual asymmetric centrifugation (DAC) to produce substantially spherical CaP, MgP, or SrP particles;
    wherein the DAC includes a plurality of discrete DAC processing steps.

14. The method of claim 13, wherein each DAC processing step is conducted with a different mixing time or mixing speed.

15. The method of claim 13, wherein a first DAC processing step is conducted at a mixing speed of greater than 1000 rpm, and a second DAC processing step is conducted at a mixing speed of less than 1000 rpm.

16. The method of claim 13, wherein each DAC processing step incorporates 800-1900 revolutions per minute for 20-85 seconds.

17. The method of claim 15, further comprising subjecting the substantially spherical CaP, MgP, or SrP particles to a second dehydration process to produce dehydrated substantially spherical CaP, MgP, or SrP particles;
- wherein the second dehydration process comprises one or more dehydration steps selected from the group consisting of heating in an oven; irradiating with microwave radiation; iteratively washing with a low vapor pressure solvent; and lyophilizing by sublimation under vacuum.

18. The method of claim 17, wherein the second dehydration process comprises washing the substantially spherical CaP, MgP, or SrP particles 3-7 times in ethanol, hexane, or acetone.

19. The method of claim 17, wherein the second dehydration process comprises heating the substantially spherical CaP, MgP, or SrP particles in an oven at a temperature above about 75° C. for a time ranging from about 18 hours to about 24 hours.

\* \* \* \* \*